United States Patent
Ashe et al.

(10) Patent No.: US 9,649,055 B2
(45) Date of Patent: May 16, 2017

(54) SYSTEM AND METHODS FOR PHYSIOLOGICAL MONITORING

(75) Inventors: Jeffrey Michael Ashe, Gloversville, NY (US); Aharon Yakimov, Niskayuna, NY (US); Siavash Yazdanfar, Niskayuna, NY (US); Milos Todorovic, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 463 days.

(21) Appl. No.: 13/435,966

(22) Filed: Mar. 30, 2012

(65) Prior Publication Data

US 2013/0261415 A1    Oct. 3, 2013

(51) Int. Cl.
| | |
|---|---|
| *A61B 5/1455* | (2006.01) |
| *A61B 5/029* | (2006.01) |
| *A61B 5/08* | (2006.01) |
| *A61B 5/024* | (2006.01) |

(52) U.S. Cl.
CPC .......... *A61B 5/14552* (2013.01); *A61B 5/029* (2013.01); *A61B 5/02427* (2013.01); *A61B 5/08* (2013.01)

(58) Field of Classification Search
CPC ............ A61B 5/14551; A61B 5/14552; A61B 5/1455; A61B 5/14532; A61B 5/0002; A61B 5/0059
USPC ..................... 600/310–344, 473, 476; 356/41
See application file for complete search history.

(56) References Cited

U.S. PATENT DOCUMENTS

| | | | |
|---|---|---|---|
| 5,803,909 A * | 9/1998 | Maki et al. .................. | 600/310 |
| 7,541,602 B2 | 6/2009 | Metzger et al. | |
| 7,826,878 B2 | 11/2010 | Alfano et al. | |
| 2002/0035315 A1* | 3/2002 | Ali et al. ..................... | 600/300 |
| 2003/0236458 A1 | 12/2003 | Hochman | |
| 2007/0078311 A1* | 4/2007 | Al-Ali et al. ................ | 600/310 |
| 2008/0312517 A1* | 12/2008 | Genoe et al. ................ | 600/323 |
| 2009/0024011 A1 | 1/2009 | Huiku | |
| 2009/0326342 A1 | 12/2009 | Huiku | |
| 2010/0081899 A1 | 4/2010 | McKenna | |
| 2010/0081901 A1* | 4/2010 | Buice et al. ................. | 600/324 |
| 2010/0081942 A1 | 4/2010 | Huiku | |
| 2010/0210926 A1 | 8/2010 | Ciancitto et al. | |

(Continued)

FOREIGN PATENT DOCUMENTS

| | | |
|---|---|---|
| EP | 0754007 A1 | 1/1997 |
| EP | 1742155 A2 | 1/2007 |

(Continued)

*Primary Examiner* — Eric Winakur
*Assistant Examiner* — Chu Chuan (JJ) Liu
(74) *Attorney, Agent, or Firm* — Joseph F. Harding; The Small Patent Law Group LLC.

(57) ABSTRACT

Embodiments of devices, methods, and non-transitory computer readable media for monitoring a subject are presented. The monitoring device includes at least one sensor configured to monitor one or more physiological parameters of a subject and a processing unit operatively coupled to the sensor. The sensor comprises a plurality of radiation sources and detectors disposed on a flexible substrate in a designated physical arrangement. The processing unit is configured to dynamically configure an operational geometry of the sensor by controlling the intensity of one or more of the radiation sources and the gain of one or more of the detectors so as to satisfy at least one quality metric associated with one or more physiological parameters of the subject.

30 Claims, 3 Drawing Sheets

(56) References Cited

U.S. PATENT DOCUMENTS

| | | |
|---|---|---|
| 2010/0249550 A1 | 9/2010 | Lovejoy |
| 2010/0280342 A1 | 11/2010 | Huiku |
| 2010/0280343 A1 | 11/2010 | Huiku |
| 2010/0331638 A1* | 12/2010 | Besko .......................... 600/323 |
| 2011/0077485 A1 | 3/2011 | Baker, Jr. et al. |
| 2011/0230739 A1* | 9/2011 | Gretz et al. ................... 600/317 |

FOREIGN PATENT DOCUMENTS

| | | |
|---|---|---|
| EP | 2301613 A1 | 3/2011 |
| EP | 2317452 A1 | 5/2011 |

* cited by examiner

SYSTEM AND METHODS FOR PHYSIOLOGICAL MONITORING

BACKGROUND

Embodiments of the present technique relate generally to physiological monitoring, and more particularly to system and methods for improving physiological parameter estimation using a multi-wavelength optical transducer array.

Continual monitoring of a patient's physiological parameters such as vital signs and/or overall health allows for accurate diagnoses and immediate alerts for life saving interventions. Particularly, routine use of multi-parameter monitors in trauma, surgery, and intensive-care unit (ICU) settings has greatly improved medical outcomes in recent times. Pulse oximeters, for example, may be used to monitor oxygen saturation (SpO2) in arterial blood. Particularly, pulse oximeters may be used to provide instantaneous measurements of arterial oxygenation to allow early detection of medical conditions such as arterial hypoxemia.

Generally, the SpO2 measurements may accurately represent the arterial oxygen saturation, even while the oxygen carrying capacity of the blood is reduced due to low overall hemoglobin concentration. However, in certain scenarios, use of only the SpO2 reading can be misleading and the oxygen supply to tissues may still be inadequate regardless of the high SpO2 value. Conventional pulse oximeters, for example, may report erroneous SpO2 measurements due to similarities in the absorption spectra of the oxygen carrying hemoglobin and dysfunctional hemoglobin (dyshemoglobin) such as Carboxyhemoglobin (HbCO) and Methemoglobin (HbMet), which are incapable of binding oxygen.

Accordingly, certain pulse oximeters have been customized to generate multiple wavelength photoplethysmographic (PPG) pulse waveforms, which may be related to tissue blood volume and blood flow at a measurement site. The customized pulse oximeters use emitters sensitive to different wavelengths for determining physiological parameters that provide useful clinical information. However, such custom devices often are suited only for a specific application, have poor adaptability to different device configurations, and/or are prohibitively expensive for routine use.

Furthermore, typical PPG-based systems are relatively large devices including a sensor attachable to the patient and the PPG device through one or more cables. Conventional PPG devices measure physiological parameters such as different hemoglobin fractions by disposing the sensor on an anatomical extremity, such as the patient's fingertip or ear. To that end, the sensor may generally comprise two or more emitter elements, each emitting radiation at a specific wavelength, connecting cables and a broad spectral band photodetector common to all emitter elements for multi-analyte measurements.

Specifically, a multiple wavelength PPG device requires measurements at a plurality of combinations of wavelengths and different emitter and detector placements to measure different substances in blood without the disruptive effects of tissue motion. A large variety of sensor types sensitive to different wavelengths, thus, may be needed to suit different subjects and different measurement sites. Accordingly, the choice of sensors and corresponding interface cables that may be used in connection with one pulse oximeter device may be rather extensive, thus impeding the portability and cost-effectiveness of the device. Additionally, the complicated reconfiguration of the pulse oximeter device for appropriately selecting and positioning the sensors and cables at the patient extremity for making a plurality of measurements may significantly add to patient discomfort.

Due to cost and complicated configuration concerns, conventional pulse oximeters are typically known to be used only in hospital environments by experienced medical professionals. Use of the pulse oximeters outside of high acuity hospital wards, however, has been limited owing to unsuitable power consumption, cost, form factor, and performance of the devices. In particular, power and performance of such physiological monitors may be limited by conventional device configurations, while corresponding measurements may often be distorted by tissue motion artifacts.

Accordingly, low-power physiological monitors conducive to portable applications and capable of mitigating motion-induced artifacts and noise for allowing accurate multi-analyte detection and monitoring are desirable.

BRIEF DESCRIPTION

Certain aspects of the present technique are drawn to a monitoring device including at least one sensor configured to monitor one or more physiological parameters of a subject and a processing unit operatively coupled to the sensor. The sensor comprises a plurality of radiation sources and detectors disposed on a flexible substrate in a designated physical arrangement. The processing unit is configured to dynamically configure an operational geometry of the sensor by controlling the intensity of one or more of the radiation sources and the gain of one or more of the detectors so as to satisfy at least one quality metric associated with one or more physiological parameters of the subject.

Certain other aspects of the present technique are directed to a method for monitoring a subject. An initial set of one or more radiation sources and one or more detectors for a particular wavelength are selected from a plurality of radiation sources and detectors disposed on a flexible substrate in a sensor in a designated physical arrangement. An initial value of one or more physiological parameters of a subject is determined by evaluating a region of interest of the subject using the initial set of radiation sources and detectors. Additionally, a quality metric associated with the initial value of the physiological parameters is estimated. Further, the operational geometry of the sensor is dynamically configured by controlling intensity of one or more of the radiation sources, gain of one or more of the detectors, or a combination thereof, to satisfy at least one quality metric associated with one or more physiological parameters of the subject.

Certain further aspects of the present technique are drawn to a non-transitory computer readable medium that stores instructions executable by one or more processors to perform a method for monitoring a subject.

DRAWINGS

These and other features, aspects, and advantages of the present technique will become better understood when the following detailed description is read with reference to the accompanying drawings in which like characters represent like parts throughout the drawings, wherein.

Figure 5:
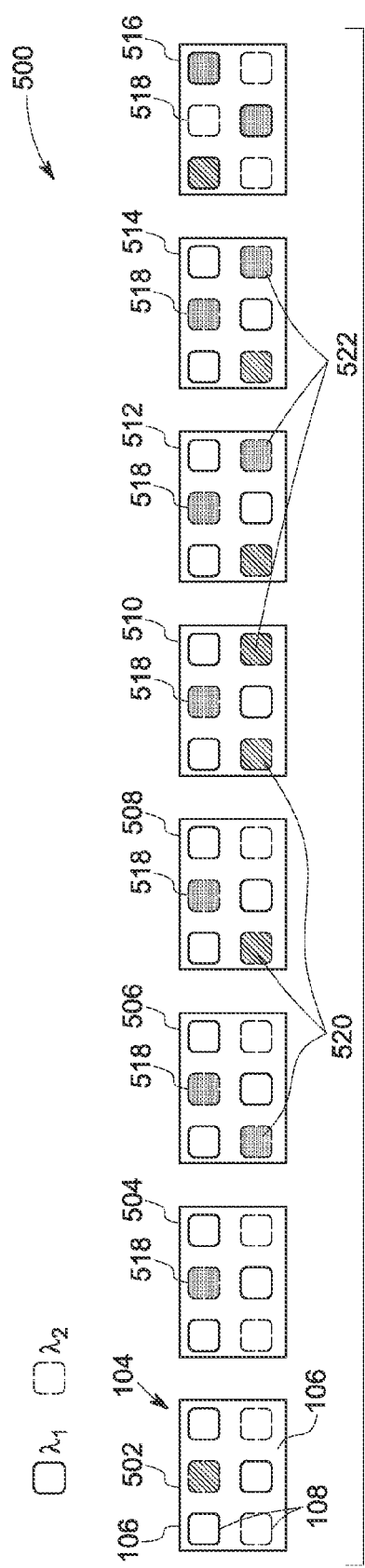
Figure 6:
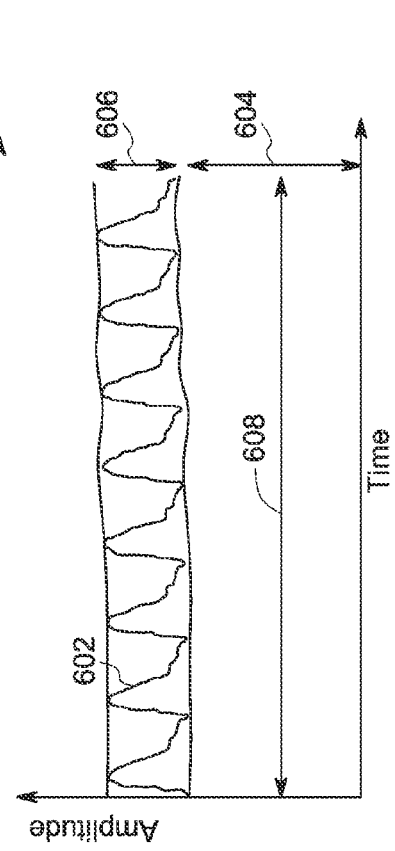

FIG. 5 illustrates exemplary configurations of an operational geometry of the sensor that may be dynamically configured to satisfy a desired quality metric, in accordance with aspects of the present technique; and FIG. 6 illustrates a graphical representation depicting an exemplary PPG waveform plotted using amplitudes of received PPG signals over time in one exemplary implementation, in accordance with aspects of the present technique.

DETAILED DESCRIPTION

The following description presents system and methods for non-intrusive monitoring one or more physiological parameters of a subject, for example a person. To that end, the physiological parameters, for example, include SpO2, one or more hemoglobin fractions, total hemoglobin concentration, HbCO concentration, methemoglobin concentration, and/or other parameters related to blood flow, blood volume and blood or tissue constituents. Particularly, certain embodiments illustrated herein describe inexpensive yet efficient methods and systems that allow continuous monitoring of the physiological parameters of the subject using a multi-wavelength optical transducer array.

For discussion purposes, embodiments of the present system are described with reference to a photoplethysmograph (PPG). However, in certain other embodiments, the present system may include any other suitable monitoring device, such as a pulse oximeter and/or a hemoglobin monitor for monitoring the subject in different operating environments. An exemplary environment that is suitable for practicing various implementations of the present system and methods is described in the following sections with reference to FIG. 1.

Figure 1:
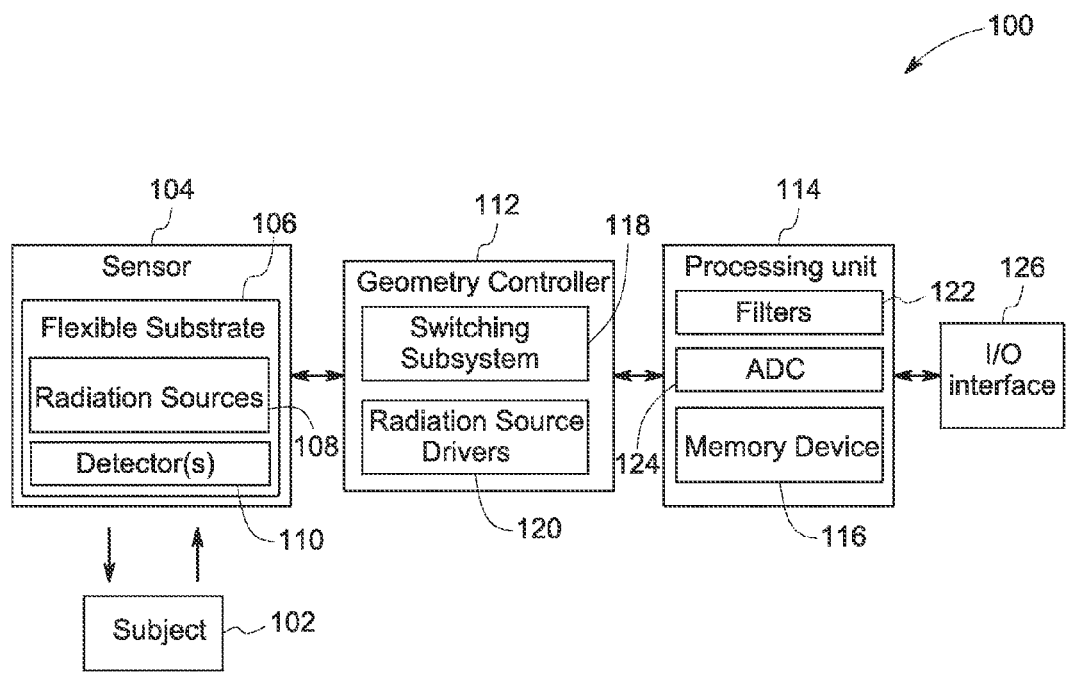
FIG. 1 is a schematic diagram of an exemplary system for monitoring one or more physiological parameters of a subject, in accordance with aspects of the present system.

FIG. 1 illustrates an exemplary monitoring system 100 for non-intrusive monitoring of one or more physiological parameters of a subject 102 (patient) such as a person. In the present description, variations of the terms "non-intrusive," and "non-invasive" monitoring are used interchangeably to refer to measuring the one or more physiological parameters with negligible direct physical contact with the patient 102. Accordingly, in one embodiment, the system 100, for example, includes a wearable pulse oximeter device for continuous monitoring of SpO2 in the subject's blood. In another embodiment, the system 100 includes a PPG sensor 104 configured to measure, for example, the total hemoglobin concentration and/or different hemoglobin fractions in the patient's blood.

To that end, the sensor 104 includes a substrate 106, and a plurality of radiation sources 108 and one or more detectors 110 disposed on the substrate 106 for monitoring the one or more physiological parameters of the patient 102. In certain embodiments, the sensor 104 is a flexible device that is generally positioned at one or more extremities of the patient. Typically, the extremities correspond to tissue regions with a rich presence of capillaries and arterioles. Such regions, for example, include distal regions of the digits, forehead, earlobe, and nose that tend to demonstrate the strongest pulse amplitudes especially in the absence of vasoconstriction, which may affect most of these locations.

Figure 2:
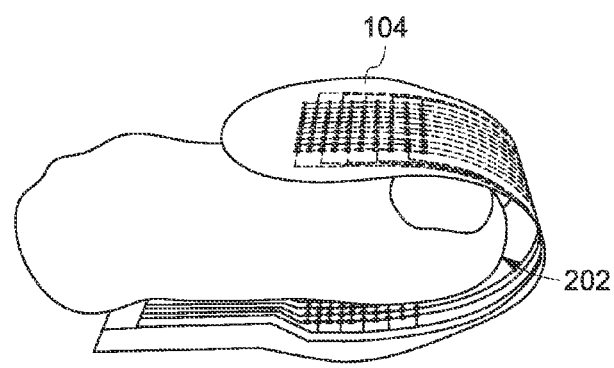
FIG. 2 is a schematic diagram illustrating an exemplary position of the sensor of FIG. 1 at a measurement site of the subject, in accordance with aspects of the present system.

FIG. 2, for example, illustrates an embodiment of the sensor 104 of FIG. 1. Particularly, FIG. 2 illustrates the sensor 104 as a lightweight and flexible device positioned around the fingertip 202 of the patient 102 where strong pulsatile signals may be observed for accurate measurements. The flexibility of the sensor 104 allows comfortable placement of the device over the patient's measurement site. Furthermore, in addition to the illustrated position of the sensor 104 configured for use on opposing surfaces on the patient's fingertip, in certain embodiments, the sensor 104 may be configured for use on adjacent surfaces at the patient's measurement site relative to the excitation.

Figure 3:
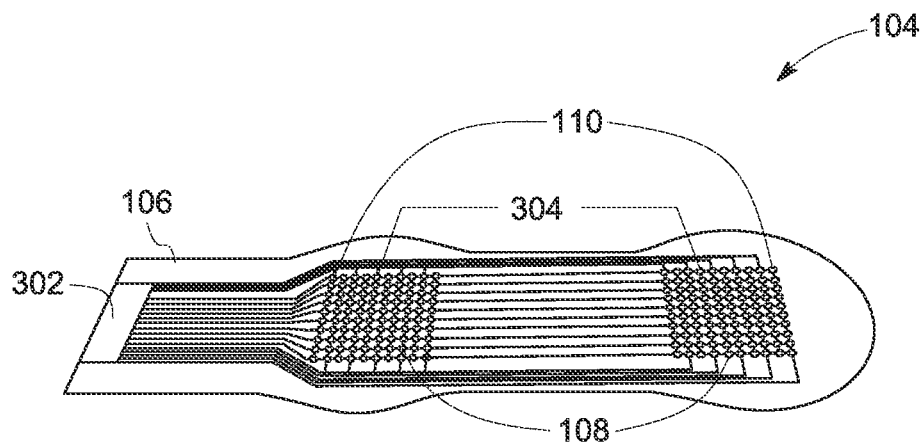
FIG. 3 is a schematic diagram of an exemplary sensor used in the system of FIG. 1 in accordance with aspects of the present system.

Further, FIG. 3 illustrates one or more exemplary components of the flexible sensor 104 for use in continuous and non-invasive monitoring of the physiological parameters of the patient 102. To that end, as previously noted, the sensor 104 includes the substrate 106, for example, including a flexible polyimide material. The sensor 104 also includes the plurality of radiation sources 108, and one or more detectors 110 disposed on the flexible substrate 106 in a designated physical arrangement. Additionally, the sensor 104 includes an interconnect 302, for example, an electrical interconnect designed to allow the radiation sources 108 and the detectors 110 to be addressed individually or by using common connections for serial or parallel configurations.

Although, FIG. 3 illustrates the sensor 104 having the flexible substrate 106, in certain embodiments, the sensor 104 may include one or more regions having a rigid substrate in addition to the flexible substrate 106. In one embodiment, for example, the substrate 106 may include one or more rigid portions in regions where the sources 108 and/or detectors 110 are disposed, while including one or more flexible portions in between the sources 108 and/or the detectors 110 for the interconnect 302.

The radiation sources 108, for example, include optical devices such as light emitting diodes (LEDs), organic-LEDs (OLEDs) and/or laser diodes of different wavelengths. In one embodiment, the wavelengths of the radiation sources 108 are in the visible and infrared (IR) spectrum. In another embodiment, the wavelengths of the radiation sources 108 are selected as per application requirements. Additionally, in certain embodiments, each of the radiation sources 108 generates radiation at one or more single wavelengths. In certain other embodiments, the radiation sources 108 are configured to generate broadband light. Certain exemplary radiation sources for use in one embodiment of the sensor 104 to allow for the multiple wavelength measurements are listed in the following table 1.

TABLE 1

| Part Number | Color | Wavelength | Bandwidth | Site | Compound |
|---|---|---|---|---|---|
| TCO12UOU | Orange | 612 nm | 20 nm | 285 m | AlInGaP |
| TCO12URU | Red | 632 nm | 20 nm | 285 m | AlInGaP |
| TCD655 | Red | 655 nm | 30 nm | 280 m | AlGaAs |
| TCM660/2 | Red | 660 nm | 25 nm | 330 m | AlGaAs |
| TCS690 | Red | 690 nm | N/A | 325 m | AlGaAs |
| TCS730 | IR | 730 nm | N/A | 325 m | AlGaAs |
| TCS760 | IR | 760 nm | N/A | 325 m | AlGaAs |
| TCS805 | IR | 805 nm | N/A | 370 m | AlGaAs |
| TCM900/10 | IR | 900 nm | 25 nm | 320 m | AlGaAs |

Further, the detectors 110 may include photodetectors 110 such as a silicon photodiode, an organic photodiode, or any other suitable detection device sensitive to single wavelengths or broadband light. Particularly, in one embodiment, a single, wide area detector may be employed to maximize light collection, thus improving performance. In another embodiment, multiple smaller area detectors may be operated simultaneously and the measured signals may be combined by analog or digital means to approximate a larger area detector.

It may be noted that the underlying science of pulse oximetry is based on a manipulation of the Lambert-Beer law, which describes the attenuation of light traveling through a mixture of absorbers. Accordingly, signals from detected light that travels through blood-perfused tissues of interest of the patient 102 can be used to estimate, for example, the underlying arterial hemoglobin composition. However, light scatters when travelling through the tissues and influences some of the simplifications made in determining the relationship between the detected attenuation and the underlying arterial hemoglobin composition.

Under most clinical circumstances, an empirical process used by the manufacturers during design to calibrate a conventional pulse oximetry system substantially accommodates the scattering in resulting readings. The quality of the plethysmographic signal, however, may still be affected by the presence of certain factors, for example, the spacing between the radiation sources 108 and the detectors 110 on the flexible substrate 106, the magnitude of the periodic increase and decrease in the tissue blood fraction, the extinction coefficient of the modulating blood volume at a particular measurement wavelength, local vessel compliance and/or venous pulsation.

Further, large pulsating vessels may also affect the quality of the plethysmographic signal. Although large pulsating vessels contribute to the optical pulse, these vessels often disrupt pulse oximetry measurements and are typically absent from common capillary measurement sites such as the distal regions of the finger or toe where strong pulsatile signals are commonly observed. Thus, the relative placement of the radiation sources 108 and the detectors 110 with respect to each other and the location of the radiation sources 108 and the detectors 110 relative to large blood vessels determines the ability of the system 100 to obtain high-quality plethysmographic signals.

Determining a suitable sensor position in conventional pulse oximetry devices, however, may require positioning and subsequent repositioning of multiple components such as emitters, detectors, housings and connecting cables at one or more measurement sites, thus distressing the patient 102. Unlike such large conventional pulse oximetry devices, embodiments of the present system 100 include low-cost disposable physiological monitors such as the flexible sensor 104 that can be attached to a desired measurement site with negligible discomfort to the patient 102. Particularly, the flexible sensor 104 allows for accurate physiological parameter measurements at multiple wavelengths without the need for further repositioning of the sensor 104 at different measurement positions.

Accordingly, in one embodiment, the sensor 104 is fabricated by disposing the radiation sources 108 and the detectors 110, sensitive to multiple wavelengths, on the flexible substrate 106 using a roll-to-roll fabrication technique. To that end, semiconducting wafer-based processing is modified for a hybrid assembly approach compatible with low-cost capabilities of roll-to-roll manufacturing to provide high performance physiological sensors at affordable costs. The hybrid approach enables use of the best-suited electronic technologies for different functions. By way of example, in the hybrid approach, silicon-bipolar for analog circuits, silicon complementary metal oxide semiconductor (CMOS) for digital circuits, Gallium Arsenide (GaAs) for high frequency operations, and/or Aluminum Gallium Arsenide (AlGaAs) for optical components may be combined in a heterogeneous manner to provide a high performance and cost-effective physiological sensor.

In another embodiment, the radiation sources 108 and detectors 110 are disposed on the flexible substrate 106 using a magnetically directed self-assembly (MDSA) technique by embedding micromagnets into the flexible substrate 106 and correspondingly embedding micromagnets into the sources 108 and detectors 110. Use of the MSDA technique allows for fabrication of the lightweight and flexible sensor 104 including a plurality of co-located radiation sources 108 and detectors 110 sensitive to one or more wavelengths. MSDA provides strong attraction, desired orientation and reliable attachment of the radiation sources 108 and the detectors 110 to the flexible substrate 106. An additional advantage of MDSA is the relative insensitivity of magnetostatic binding forces towards external perturbations such as surface contamination, trapped charge, conductivity, and pH, presence of other non-magnetic materials or nearby binding sites.

In a further embodiment, the radiation sources 108 and detectors 110 are disposed on the flexible substrate 106 in a designated physical arrangement using electrical and/or mechanical means. Although only few exemplary fabrication techniques are described herein, in certain other embodiments, the sensor 104 may be fabricated using any other conventional manufacturing technique that allows for fabrication of the lightweight and flexible sensor 104 including a plurality of co-located radiation sources 108 and detectors 110 sensitive to one or more wavelengths.

Further, in certain embodiments, the sensor 104 is fabricated such that the radiation sources 108 and detectors 110 are disposed on the flexible substrate 106 in a designated physical arrangement to allow multiple measurements without physically moving the sensor 104 to a different measurement position, in one embodiment, for example, the radiation sources 108 and detectors 110 are arranged as a pixelated optical transducer array of large area (for example, of about 1 centimeter squared ($cm^2$)) on the flexible substrate 106 to reduce tissue motion artifacts and improve light collection efficiency. In another embodiment, the radiation sources 108 and detectors 110 sensitive to different wavelengths, for example, are embedded individually or in specific groups in an array in the flexible substrate 106. In certain other embodiments, the radiation sources 108 and the detectors 110 sensitive to different wavelengths are placed within the array in an interleaving manner. In further embodiments, the distances between the radiation sources 108 and the detectors 110 are configured to be of various lengths to allow different depths of light penetration into the target tissue.

FIG. 3, for example, illustrates an exemplary physical arrangement of the radiation sources 108 and the detectors 110 on the flexible substrate 106. Particularly, FIG. 3 depicts the radiation sources 108 and detectors 110 arranged in two 10×10 arrays 304 on the flexible substrate 106. Although FIG. 3 illustrates two 10×10 arrays 304, in certain embodiments, a fewer or greater number of the radiation sources 108 and detectors 110 may be incorporated onto an appropriately sized flexible substrate to extend the sensor functionality to different monitoring applications.

In certain embodiments, for example, the radiation sources 108 and detectors 110 arranged on the flexible substrate 106 to operate in a reflectance and/or a transmission mode. Particularly, in one embodiment, the sensor 104 operates in transmission mode (see FIG. 2) where the radiation sources 108 and detectors 110 are operated on opposite sides of the tissue, for example, for measuring light transmission through a finger or an earlobe. Alternatively, the sensor operates in reflectance mode where the radiation sources 108 and detectors 110 are operated on the same side of the tissue, for example, for measuring light reflection from the forehead or the sternum. In a further embodiment, the sensor 104 operates in a combined mode where the radiation sources 108 and detectors 110 are operated on both sides of the tissue to simultaneously measure reflectance and transmission signals.

Use of the collocated radiation sources 108 and detectors 110 operating at multiple wavelengths, thus, allows for measurement of different optical absorption and scattering characteristics of the target issue and corresponding constituents such as cells, blood, and interstitial fluid. Additionally, presence of a plurality of the radiation sources 108 and the detectors 110 capable of operating at multiple wavelengths allows for redundancy, thus improving the reliability of the system 100. Particularly, in case of failure of one or more components, the system 100 may selectively operate the remaining radiation sources 108 and the detectors 110 so as to provide the desired gain and intensity characteristics for measuring physiological parameters of interest.

Further, in certain embodiments, optically opaque barrier materials (not shown) may be used to prevent direct coupling of adjacent radiation sources 108 and detectors 110 using an under-fill or intra-fill technique to further ensure the accuracy of the measurements. Additionally, use of the large area, arrayed radiation sources 108 and detectors 110 reduces distortions caused by the tissue motion typically observed in single source, single detector point-to-point measurements. The resulting multiple wavelength measurements, thus, can be used to improve pulse oximetry measurements and in many other multi-parameter spectroscopic applications.

Particularly, certain spectroscopic applications may often require multiple wavelength measurements for estimating different hemoglobin fractions or to maximize sensitivity by improving the quality metrics such as signal-to-noise ratio (SNR) of a resulting waveform. Conventional pulse oximetry devices, however, may require extensive rearrangement of corresponding sources 108 and the detectors 110 for multiple wavelength measurements. In particular, the sources 108 and the detectors 110 may need to be physically moved to a different measurement site, for example, for mitigating the disruptive effects caused due to the presence of a large pulsating blood vessel. Such repeated rearrangements, however, may cause discomfort to the patient 102 and may require the presence of a trained medial professional.

In contrast to such conventional pulse oximetry devices that require extensive rearrangement, the system 100 of FIG. 1 allows for dynamic reconfiguration of the operational geometry of the radiation sources 108 and the one or more detectors 110 in the sensor 104 without physically moving the sensor 104 to different measurement positions. As used herein, the term "operational geometry" refers to a subset of the radiation sources 108 and detectors 110, selected from the plurality of radiation sources 108 and detectors 110 disposed on the flexible substrate 106, which when operational, provide desired location and intensity characteristics.

Accordingly, in an embodiment such as illustrated in FIG. 1, the system 100 includes a geometry controller 112 coupled to a processing unit 114 that adaptively reconfigures the operational geometry of the radiation sources 108 and the detectors 110 to satisfy one or more quality metrics of the physiological parameters of interest. Accordingly, in certain embodiments, the processing unit 114 estimates the quality metrics, such as, SNR, amplitude or an alternating current-to-direct current (AC-to-DC) ratio of an output signal measured at a particular wavelength. The estimated quality metrics are then compared against corresponding thresholds or desired values. If the quality metrics are outside the corresponding thresholds, the processing unit 114 uses the geometry controller 112 to reconfigure the operational geometry of the sensor 104 (sensor geometry) to optimize the quality metrics.

To that end, in one embodiment, the geometry controller 112 includes, for example, a switching subsystem 118 including a plurality of switches and one or more radiation source drivers 120 coupled to the sensor 104 through one or more interfaces such as the interconnect 302 illustrated in FIG. 3. The drivers 120, in one embodiment, include a self-contained power supply having outputs matched to the electrical characteristics of the corresponding radiation sources 108. In certain embodiments, the drivers 120 may include more than one channel for separate control and/or adjustment of not only the activation and deactivation, but also the gain and/or intensity of the different radiation sources 108 and detectors 110.

In one embodiment, for example, the system 100 employs the drivers 120 along with the plurality of switches to selectively operate the radiation sources 108 and the detectors 110 either individually, in specific groups, and/or by using common connections for serial or parallel configurations. In another embodiment, the processing unit 114 adaptively reconfigures the sensor geometry to optimize the excitation patterns by selectively operating only those radiation sources 108 and the detectors 110 that contribute significantly to the plethysmographic signal. Particularly, in certain embodiments, the processing unit 114 selects the radiation sources 108 and the detectors 110 that optimize the optical paths through the target tissue to minimize the effects of large blood vessels and other large static absorbers.

In one embodiment, the processing unit 114 performs the optical path optimization using pre-determined information stored in a memory device 116. In certain embodiments, the memory device 116 may include storage devices such as RAM, ROM, disc drive, solid-state drive and/or flash memory. Further, the processing unit 114 includes, for example, one or more microprocessors, microcomputers, microcontrollers, field programmable gate arrays, application specific integrated arrays, or any other suitable device for performing the optimization. Particularly, the processing unit 114 optimizes the optical paths so as to improve the quality metric of the physiological parameters of interest and/or the power efficiency of directing and collecting transmitted or reflected light.

To that end, in certain embodiments, the processing unit 114 employs one or more photon transport models to investigate the effects of the placement of the radiation sources 108 and the detectors 110 on the quality of the output signals. Photon transport models, for example, may include Monte Carlo simulations, finite-difference time domain models, as well as analytical solutions and diffusion approximations of radiative transfer equations.

Particularly, in one embodiment, the processing unit 114 uses the Monte Carlo methods to simulate photon transport for multiple wavelengths. The processing unit 114, for example, uses optical path length data corresponding to each wavelength to account for the non-linearity of photon transport through the tissue while performing multi-analyte measurements. The processing unit 114 then optimizes the source-detector configuration based on the specific geometry (transmission or reflection) of the sensor 104 using Monte Carlo simulations. Subsequently, based on the quality metrics estimated for the initial measurements, the processing unit 114 reconfigures the sensor geometry to operate the radiation sources 108 and/or the detectors 110 as large area, or distributed devices that maximize optical generation and light capture efficiency, while reducing tissue motion artifacts.

In certain embodiments, the processing unit 114 employs the reconfigured sensor geometry corresponding to one wavelength for determining the geometry configurations for the other wavelengths. Here, it may be noted that spectroscopic applications entailing measurement of different optical absorption and scattering characteristics of a target tissue and its constituents often require measurements at multiple wavelengths. To that end, in one embodiment, the processing unit 114 iteratively operates one or more combinations of the radiation sources 108 and the detectors 110 of different wavelengths through substantially the same path through the target tissue. In every iteration, the incident radiation undergoes attenuation, which may be dependent, among other things, on the wavelength of the light, the type and concentration of the substances within the target tissue, and the volume changes in the arterial bloodstream.

The impinging radiation is then received and processed by the detectors 110 for further use. In one embodiment, for example, the received signal is band-pass filtered using one or more filters 122 to segregate the signal information from noise, interference and/or motion artifacts. The filtered signals are then appropriately amplified and converted into digital signals, for example, using an analog-to-digital converter (ADC) 124 for further evaluation. In certain embodiments, the processing unit 114 analyzes the digitized signals using one or more stored procedures to determine if the quality of the physiological parameter measurements is within one or more desired or a designated threshold values.

As previously noted, based on the estimated quality metrics, the processing unit 114 may adaptively reconfigure the geometry of the radiation sources 108 and the detectors 110 to optimize the physiological parameter measurements for a particular wavelength over one or more iterations. The processing unit 114 then uses the reconfigured geometry to determine suitable sensor geometry for other wavelengths so as to estimate values of the physiological parameters, such as the oxygen saturation, heart rate, blood pressure, cardiac output, respiration and/or hemoglobin concentration.

In one embodiment, the processing unit 114 the displays the estimated values on an input-output (I/O) interface 126 coupled to the system 100. In another embodiment, the processing unit 114 stores the determined information for later review and analysis in the memory device 116. In certain other embodiments, the processing unit 114 communicates the determined information to another location such as local or remotely located hospital information system over a communications link (not shown). To that end, the communication link, for example, may include wired networks such as LAN and cable, wireless networks such as WLAN, cellular networks, satellite networks, and/or short-range networks such as ZigBee wireless sensor networks.

Additionally, in certain embodiments, the processing unit 114 may also generate an alert through the I/O interface 126 if values of any of the physiological parameters are determined to be outside designated thresholds. Particularly, in one embodiment, the processing unit 114 generates an audio and/or a visual alert such as flashing lights, sounds an alarm, and/or sends a voicemail, text messages and/or email to a mobile device of appropriate personnel and/or to another health information system through a wired and/or wireless communications link.

Embodiments of the system 100 allow for selective excitation of the sensor components to ensure that only the necessary subset of all available radiation sources 108 are used at any time, thus minimizing the power consumption of the entire PPG module. Similarly, on the detection side, the selective use of the detectors 110 allows for a desired detection efficiency by effectively increasing the detection area, while at the same time keeping the detectors 110 that do not significantly contribute to the overall signal off to reduce power consumption.

Furthermore, the reconfigurable geometry of the sensor 104 also minimizes the effects of large static absorbers, which negatively affect the quality of the signals and consequently the accuracy of the estimated physiological parameters. The overall adaptive nature of the excitation/detection patterns, thus, enables the collection of high quality signals with the minimal power consumption to allow fabrication of low-power battery-operable monitoring devices that provide greater signal fidelity, ease of usage and patient comfort.

Although FIG. 1 illustrates an embodiment of the system 100 as a stand-alone device, in certain embodiments, the system 100 can be operationally coupled with other devices and systems that can be non-invasive and/or invasive and provide additional data that can be processed by the processing unit 114 or by some central processing section to enable more comprehensive monitoring, assessment, diagnosis, and/or preventative care. The functioning of an exemplary system for monitoring the physiological parameters of a subject and assessing a health condition of the patient 102, in accordance with aspects of the present technique, is described in greater detail with reference to FIG. 4.

Figure 4:
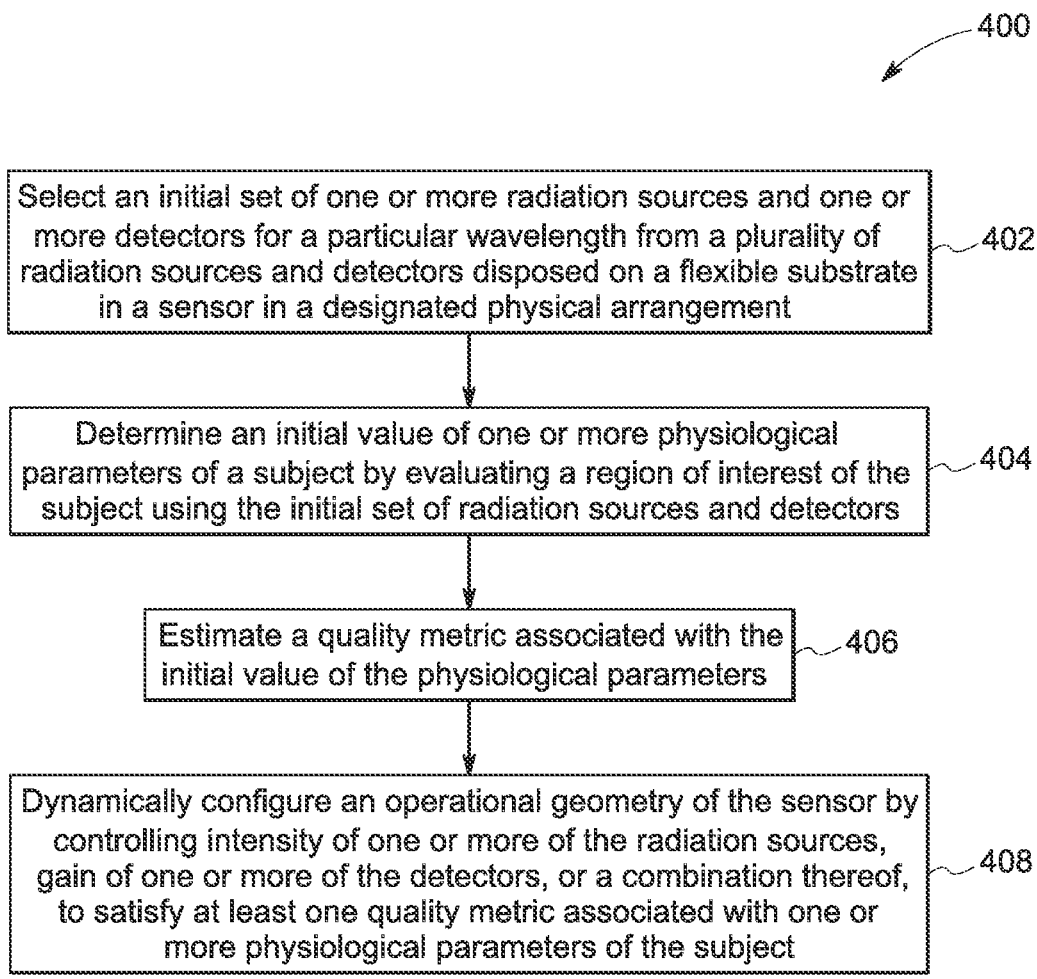
FIG. 4 is a flow chart illustrating an exemplary method for monitoring one or more physiological parameters of the subject, ire accordance with aspects of the present technique.

FIG. 4 illustrates a flow chart 400 depicting an exemplary method for monitoring the physiological parameters of a subject using a dynamically configurable, multi-source, multi-detector arrayed PPG sensor. To that end, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Certain embodiments of the exemplary method may also be practiced in a distributed computing environment where optimization functions are performed by remote processing devices that are linked through communications network. In the distributed computing environment, the computer executable instructions may be located in both local and remote computer storage media, including memory storage devices. The computer executable instructions, for example, may be stored or adapted for storage on one or more tangible, machine readable media such as data repository chips, local or remote hard disks, optical disks (compact disks or digital versatile disks), solid state devices, or other suitable media, which may be accessed by a processor-based system to execute the stored instructions.

Further, in FIG. 4, the exemplary method is illustrated as a collection of items in a logical flow chart, which represents operations that may be implemented in hardware, software, or a combination thereof. In the context of software, the blocks represent computer instructions that, when executed by one or more processing systems, perform the recited operations. The order in which the exemplary method is described is not intended to be construed as a limitation, and any number of the described items may be combined in any order to implement the exemplary method disclosed herein, or an equivalent alternative method. Additionally, certain items may be deleted from the exemplary method without departing from the spirit and scope of the subject matter described herein. For discussion purposes, the exemplary method is described with reference to the implementations of FIGS. 1-3.

In one embodiment, a healthcare monitoring system, such as the system 100 of FIG. 1, continually monitors one or more physiological parameters of a subject. To that end, the monitoring system 100 employs, for example, a dynamically configurable, multi-source, multi-detector arrayed PPG sensor 104 such as the sensor 104 of FIG. 1. As described with reference to FIGS. 1-3, the PPG sensor 104 includes a plurality of co-located and independently operable radiation sources 108 and detectors 110 of different wavelengths disposed on the flexible substrate 106 in a designated physical arrangement for physiological monitoring.

Traditional PPG devices measure oxygen saturation (SpO2) in arterial blood non-invasively and continuously by a sensor attached to the finger or ear. Clinically, SpO2 has been used as an indication of the oxygen supply to tissues. Particularly, high oxygen saturation and strong and regular peripheral pulsation are clinical signs that have been used to reflect adequate oxygenation of blood in the lungs and sufficient cardiac function to supply oxygen rich blood to tissues. However, use of only the SpO2 reading can be misleading and the oxygen supply to tissues may still be inadequate regardless of the high SpO2 value.

Particularly, conventional pulse oximeters may report high SpO2 values even though the oxygen carrying capacity is low. These erroneous SpO2 measurements may occur due to the similarities in the absorption spectra of the oxygen carrying hemoglobin and the dysfunctional hemoglobin (dyshemoglobin), such as HbCO and HbMet, which are incapable of binding oxygen. In certain scenarios, a high SpO2 reading even in the absence of dyshemoglobin does not guarantee sufficient oxygenation of tissues if the total hemoglobin concentration is low. Conventional noninvasive pulse oximeters, thus, may not be able to quantify the amount of oxygen delivered and utilized by the tissue consistently, and therefore, may require additional tissue and/or blood samples to confirm the adequacy of tissue oxygenation.

Unlike such conventional monitoring devices, the dynamically configurable, multi-source, multi-detector arrayed PPG sensor 104 described herein finds uses beyond traditional pulse-oximetry applications for assessing a variety of health conditions using multiple wavelength measurements. In one embodiment, for example, the PPG sensor 104 may be used as a potential diagnostic tool to detect clinically significant hypovolemia before the onset of cardiovascular decompensation.

To that end, at step 402, the processing unit 114 selects an initial set of one or more radiation sources and detectors sensitive to a particular wavelength from the plurality of radiation sources 108 and detectors 110 embedded in the flexible substrate 106 in a designated physical arrangement, for example, as depicted by the array 304 of FIG. 3. The overall absorption is typically higher at lower wavelengths. Accordingly, in one embodiment, the processing unit 114 selects the initial set of one or more radiation sources 108 and detectors 110 that are sensitive to a lower wavelength, for example, at about 630 nm. In certain embodiments, the processing unit 114 uses a designated wavelength typically used to measure a specific physiological parameter being monitored as the initial wavelength. In certain other embodiments, the processing unit 114 may use a user-supplied wavelength as the initial wavelength.

Further, at step 404, the processing unit 114 configures the monitoring system 100 to use the initial set of radiation sources 108 to irradiate the target tissue. An initial set of detectors 110 receive and process the impinging radiation for further evaluation. In one embodiment, for example, the received signal is filtered, amplified and converted into digital signals for determining an initial value of the one or more physiological parameters of the subject. The physiological parameters, for example, may include oxygen saturation, heart rate, cardiac output, respiration, and/or other parameters related to blood flow, blood volume and blood or tissue constituents.

Further, at step 406, the processing unit 114 estimates a quality metric associated with the initial values of the physiological parameters. Particularly, the processing unit 114 may estimate the quality metrics continuously or periodically for assessing the quality of the measured physiological parameter values. In one embodiment, for example, the processing unit 114 monitors the SNR of the determined physiological parameter values continuously. In another embodiment, the processing unit 114 determines the optical power received at the receiving end, or the amplitude of the received signal to determine corresponding quality metrics. In certain other embodiments, the processing unit 114 uses the AC component, or the ratio of the AC component to the DC component of the signal (or the normalized signal) for one or more wavelengths to determine the quality metric associated with the physiological parameter of interest such as a relative concentration of the hemoglobin species in the blood.

Additionally, the processing unit 114 may compare the determined quality metrics with the corresponding threshold or desired values defined as per application and/or user specified requirements. In certain embodiments, the processing unit 114 may determine if two or more quality metrics such as the optical power and the corresponding AC-to-DC component of the output signal are within the designated thresholds. If the quality metrics determined from the initial configuration are outside designated thresholds, at step 408, the processing unit 114 dynamically reconfigures the geometry by selectively operating one or more further radiation sources 108 and/or one or more detectors 110 selected from the plurality of radiation sources 108 and detectors 110.

Particularly, the processing unit 114 reconfigures the sensor geometry to satisfy the quality metric associated with values of the physiological parameters measured using the further radiation sources 108 and detectors 110. In one embodiment, for example, the processing unit 114 reconfigures the sensor geometry such that the SNR of the physiological parameters measured using the further radiation sources 108 and detectors 110 is within a desired range. In another embodiment, the processing unit 114 may reconfigure the geometry such that the output signals have a desired AC-to-DC component while the power consumption of the monitoring system 100 is minimized.

One or more suitable techniques may be employed to optimize the sensor geometry. In one embodiment, for example, the processing unit 114 employs Monte Carlo simulations to determine the most appropriate combination of the radiation sources 108 and the detectors 110 that allow for optimization of the desired quality metrics. The processing unit 114 performs Monte Carlo simulations, for example, to investigate the effects of the placement of the arrayed radiation sources 108 and detectors 110 on the quality of the signals. The simulations then allow the processing unit 114 to optimize the source-detector separation based on the specific geometry (transmission or reflection) of the PPG sensor 104. By way of example, in an exemplary implementation, Monte Carlo simulations were performed to obtain the predicted plethysmographic signals for the wavelengths 613 nm, 632 nm, 660 nm, 690 nm, 730 nm, 760 nm, 800 nm and 900 nm.

Accordingly, in one embodiment, the processing unit 114 selects the sensor wavelengths for adaptive reconfiguration from among the available radiation sources 108 of high emissivity. Particularly, the wavelengths are selected so as to provide good coverage over the range in which the tissue transmission is high enough, for example, from about 600 to about 1000 nm in a specific application. Additionally, in certain embodiments, the center wavelengths are optimized to locate at, or proximal the isobestic wavelengths of the physiological parameter of interest, for example, hemoglobin derivatives. The wavelengths are further optimized to avoid regions where the changes in the total blood and tissue absorptions are prominent, thus minimizing the effects of possible wavelength shifts in the radiation sources 108.

Furthermore, in certain embodiments, the processing unit 114 reconfigures the sensor geometry to operate the radiation sources 108 and/or the detectors 110 as large area or distributed devices so as to maximize the efficiency of directing and collecting transmitted or reflected light. In an alternative embodiment, a single large area detector may be used to maximize light collection. By way of example, FIGS. 5 and 6 illustrate exemplary reconfigurations of the sensor geometry using the method of FIG. 4 for measuring physiological parameters such as HbCO concentration in the patient's blood.

Particularly, FIG. 5 illustrates certain exemplary configurations 500 of the operational geometry of the sensor 104 that may be dynamically configured to satisfy a desired quality metric for measuring arterial blood components of interest. In the embodiment illustrated in FIG. 5, the sensor 104 includes six radiation sources 108 and one or more detectors (not shown) capable of receiving different wavelengths emitted by the radiation sources 108.

In one embodiment, for example, three of the radiation sources 108 are configured to emit a first wavelength $\lambda_1$, whereas the other three radiation sources 108 are configured to emit a second wavelength $\lambda_2$. Further, the radiation sources 108 are arranged on the flexible substrate 106, for example, in a symmetrical arrangement such that an optimal operating configuration at one wavelength may be used as a baseline operating configuration for determining optimal configurations for other wavelengths. To that end, in one embodiment, the processing unit 114 iteratively reconfigures operational geometry of the sensor 104 into different configurations 502-516 by selectively operating the radiation sources 108 and detectors to maximize the quality metric.

FIG. 6 illustrates a graphical representation 600 depicting an exemplary PPG waveform 602 plotted using the amplitude of received PPG signals over time in an exemplary implementation. Particularly, the PPG waveform 602, as illustrated in FIG. 6, includes a DC component 604 attributed to the reflectance, absorbance or transmittance of light from static tissues and fluids within the optical path. The PPG waveform 602 also includes an AC component 606 attributed to the reflectance, absorbance or transmittance of light from pulsating arterial blood. In the exemplary implementation, quality metric is chosen to maximize the AC-to-DC ratio in order to increase sensitivity to arterial blood components.

To that end, as illustrated in the configuration 502 of FIG. 5, for example, a first radiation source 518 of the first wavelength $\lambda_1$ is operated and the resulting quality metric is observed over an epoch duration 608 of several arterial pulses. The processing unit 114 then reconfigures sensor geometry into a configuration 504 so as to adjust the intensity of the first radiation source 518 to determine one or more operational settings at which the quality metric is maximized. Further, the processing unit 114 reconfigures the sensor geometry into a configuration 506, in which a second radiation source 520 of the first wavelength $\lambda_1$ is operated simultaneously with the first radiation source 518 and the corresponding quality metric is observed.

In another configuration 508, the intensity of the second radiation source 520 is adjusted to determine the operational settings at which the quality metric is maximized. Further, in a subsequent configuration 510, the sensor geometry is reconfigured by operating a third optical source 522 of the first wavelength $\lambda_1$ simultaneously with the first and second radiation sources 518, 520 and determining the corresponding quality metric. Similarly, at a configuration 512, the intensity of the third radiation source 522 is adjusted to determine the operational settings of the sensor 104 at which the AC-to-DC ratio is maximized.

A final operating configuration 514 then becomes the baseline configuration for the first wavelength, $\lambda_1$. Further, in certain implementations, the corresponding symmetric operational configuration may be used as a baseline configuration for the second wavelength, $\lambda_2$. The processing unit 114 estimates the quality metric over time, while adjusting the intensities of the radiation sources 518, 520 and 522, either independently or simultaneously, so as to maximize the quality metric during the course of operation. Although the embodiment described with reference to FIG. 5 describes the quality metric for the first and second wavelengths $\lambda_1$ and $\lambda_2$ to be in a symmetric configuration, in certain implementations, the quality metrics may differ from a baseline depending on the continual measurements.

Adaptive reconfiguration of the geometry, thus, allows optimization of the excitation patterns by selectively operating only those radiation sources 108 and the detectors 110 that contribute significantly to the plethysmographic signal. It may be noted that much of the power inefficiency in a conventional PPG device is due to excitation of all the radiation sources and signal processing of the measured signals. Accordingly, selective operation of a subset of the sensor components, in one embodiment, minimizes the power consumption to allow use of a ubiquitous, wearable and battery-powered monitoring device.

Further, in certain embodiments, the processing unit 114 adaptively reconfigures the sensor geometry continually, periodically, or when the desired quality metrics fall or remain outside their designated thresholds for more than a designated period of time, thus further improving the power consumption. Additionally, selective operation of a subset of the sensor components optimizes the optical path, in turn minimizing the effects of large blood vessels and other large static absorbers on the output physiological parameter values measured using a particular wavelength. The optical path optimization reduces motion artifacts to allow for high-fidelity signal measurements.

Many spectroscopic applications, however, require measurements from multiple wavelengths to estimate a variety of hemoglobin fractions for assessing different and complicated health conditions of the patient. The fundamental principle of photoplethysmography is that light of different wavelengths traverses the same path through the target tissue so as to interrogate the same volume for obtaining accurate physiological parameter measurements. The collocation of the radiation sources 108 and detectors 110 on the flexible substrate allows for similar path lengths through the target tissue. Accordingly, in certain embodiments, the processing unit 114 employs the reconfigured geometry configurations from one wavelength to determine the geometry configuration for other wavelengths of interest for multi-analyte measurements.

Particularly, in one embodiment, the processing unit 114 analyzes the alterations in the PPG waveform measured at different wavelengths to track progressive reductions in central blood volume. In another embodiment, PPG observations measured from the finger, ear, and forehead may be analyzed to extract features such as pulse amplitude, pulse width, and area under the-curve for each cardiac cycle. During certain exemplary implementations, it was determined that these features are strongly correlated to stroke volume, and therefore, may provide observable changes prior to profound decreases in arterial blood pressure that may to baseline after the removal of the hemodynamic challenge.

Accordingly, the embodiments of the arrayed, multi-wavelength PPG sensor 104, such as described herein, may be used to extend these clinical insights for the early detection of acute hemorrhage and subsequent circulatory collapse in an emergency, a hospital or a remote point-of-care environment. Similarly, embodiments of the arrayed PPG sensor 104 may further be used to make accurate multiple wavelength measurements that aid in early detection, monitoring and treatment of a variety of other vascular diseases. These vascular diseases, for example, include peripheral vascular disease, arterial disease, hemorrhage, hemodynamic shock, carbon monoxide poisoning, anemia, arterial compliance and aging, endothelial function, vasospastic conditions such as Raynaud's phenomenon, microvascular blood flow and tissue viability.

Use of a disposable, multiple wavelength sensor allows for non-invasive and continuous monitoring of a patient's physiological parameters in traditional hospital environments and in extended environments such as at a site of accident, in an ambulance or in a war situation, thus saving lives and expediting recovery from injury and illness. Particularly, the PPG sensor 104 allows for improvements in general clinical practice by providing easy and immediate access to patient's total hemoglobin concentration and composition in emergency and acute care, specifically in the areas of blood transfusion and fluid management. Accurate total hemoglobin and dyshemoglobin measurements greatly improve patient safety and quality of care, because the oxygenation can be assessed and treated immediately in a cost-effective and user-friendly manner.

Further, the PPG sensor's continuous monitoring ability may be used to improve management of bleeding patients by adopting informed blood transfusion strategies, thus resulting in fewer complications during surgery and intensive care. Additionally, the risk of arterial catheterization and infection is mitigated by using the continuously monitored information. In certain embodiments, use of the portable PPG sensor 104 allows for immediate diagnosis and treatment of carbon-monoxide poisoned patients in ambulatory or emergency room scenarios. In certain other embodiments, the absence of complicated source-detector rearrangements for multiple wavelength measurements in the PPG sensor 104 allows for painless hemoglobin and hematocrit tests.

Embodiments of the monitoring system and methods disclosed hereinabove, thus, provide a non-invasive, inexpensive and efficient technique for monitoring and evaluating the physiological parameters, and in turn the health of a subject. Particularly, the portable nature of the monitoring system described herein greatly improves medical outcomes by expanding physiological monitoring to previously "unmonitorable" settings, for example, in the battlefield. Use of heterogeneous, co-located multiple wavelength radiation sources and detectors allows continuous monitoring of a plurality of physiological parameters and corresponding health conditions, while improving infection control through the use of a single-patient-use disposable monitoring system.

Further, the adaptive configuration of the sources and detectors allows for multiple wavelength measurements that allow extension to several other clinical applications without causing undue patient discomfort. In particular, selective operation of the sources and detectors may be used to optimize the power consumption and ensuring a desired quality of physiological parameter measurements. Additionally, the portability of the monitoring system improves accessibility to medical diagnostic capabilities in remote locations in a cost effective manner, thus minimizing hospital stay while also allowing automatic recording, assessing and transmitting vital medical information to a central/remote healthcare system for storage and evaluation.

Although specific features of various embodiments of the invention may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and techniques.

While only certain features of the present invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A monitoring device, comprising:
   at least one sensor configured to monitor one or more physiological parameters of a subject, wherein the sensor comprises a plurality of radiation sources and detectors disposed on a flexible substrate in a designated physical arrangement;
   a processing unit operatively coupled to the sensor, wherein the processing unit is configured to:
   dynamically configure an initial operational geometry of the sensor for an initial wavelength by controlling the intensity of one or more of the radiation sources and the gain of one or more of the detectors until a threshold value of at least one quality metric associated with one or more physiological parameters of the subject is satisfied;
   determine a revised configuration of operational geometry of the sensor for each of plural additional wavelengths using Monte Carlo simulations at each of the plural additional wavelengths, wherein the processing unit is configured to perform the Monte Carlo simulations to determine resulting signal quality based on placement of the radiation sources and detectors for plural configurations and to select the revised configuration based on the determined resulting signal quality; and
   obtain measurements of the one or more physiological parameters at each of the plural additional wavelengths using the corresponding revised configuration for each of the plural additional wavelengths, without physically moving the sensor to a different measurement position.

2. The monitoring device of claim 1, wherein the operational geometry of the sensor comprises a subset of one or more radiation sources and detectors selected from the plurality of radiation sources and detectors disposed on the flexible substrate, which when operational, provide desired location and intensity characteristics, and wherein at least one of the revised configurations uses a subset that is symmetric with a subset used for the initial operational geometry.

3. The monitoring device of claim 1 being a multi-wavelength photoplethysmograph device.

4. The monitoring device of claim 1 being a multi-source multi-detector arrayed photoplethysmograph device.

5. The monitoring device of claim 1, wherein the plurality of radiation sources and detectors are disposed on the flexible substrate using a roll-to-roll assembly technique.

6. The monitoring device of claim 1, wherein the substrate is a flexible polyimide substrate.

7. The monitoring device of claim 1, wherein the sensor comprises a pixelated optical transducer comprising the plurality of radiation sources and detectors arranged in an array on the flexible substrate.

8. The monitoring device of claim 1, wherein the radiation sources are disposed on the flexible substrate at a plurality of distances from the detectors to allow different depths of light penetration into a region of interest of the subject.

9. The monitoring device of claim 1, wherein the radiation sources comprise sources configured to generate radiation at a plurality of wavelengths.

10. The monitoring device of claim 9, wherein the radiation sources comprise one or more light emitting diodes, one or more organic light emitting diodes, one or more laser diodes, or combinations thereof.

11. The monitoring device of claim 1, wherein the detectors comprise organic photodetectors.

12. The monitoring device of claim 1, wherein a response curve of the detectors covers a spectrum band of interest.

13. The monitoring device of claim 1, wherein the quality metric comprises signal-to-noise ratio, an amplitude or an alternating current-to-direct current ratio of an output signal measured at a particular wavelength.

14. The monitoring device of claim 1, wherein one or more physiological parameters comprise one or more hemoglobin fractions.

15. The monitoring device of claim 1, wherein one or more physiological parameters comprise one or more of oxygen saturation, blood flow, blood volume, carboxyhemoglobin, methemoglobin, total hemoglobin, heart rate, cardiac output, respiration, or combinations thereof.

16. The monitoring device of claim 1, wherein the processing unit is configured to dynamically configure the operational geometry of the sensor by selectively operating one or more of the radiation sources and one or more of the detectors to improve the optical path between the one or more radiation sources and one or more of the detectors to improve the signal-to-noise ratio of the one or more physiological parameters of the subject.

17. The monitoring device of claim 1, wherein the processing unit is configured to dynamically configure the operational geometry of the sensor by selectively operating one or more of the radiation sources and one or more of the detectors that minimize effects of large blood vessels or static absorbers.

18. The monitoring device of claim 1, wherein the processing unit is configured to dynamically configure the operational geometry of the sensor by selectively operating one or more of the radiation sources and one or more of the detectors that minimize power consumption.

19. The monitoring device of claim 1, wherein the processing unit is configured to dynamically configure the operational geometry of the sensor using a photon transport model.

20. The monitoring device of claim 1, wherein the processing unit comprises a geometry controller configured to selectively operate one or more of the radiation sources and one or more of the detectors, wherein the geometry controller comprises one or more switching subsystems.

21. The monitoring device of claim 1, wherein the processing unit is configured to operate the monitoring device in transmission mode by selectively operating one or more of the radiation sources and one or more of the detectors such that the radiation sources and the detectors are disposed on opposite sides of a region of interest of the subject.

22. The monitoring device of claim 1, wherein the processing unit is configured to operate the monitoring device in reflectance mode by selectively operating one or more of the radiation sources and one or more of the detectors such that the radiation sources and the detectors are disposed on the same side of a region of interest of the subject.

23. The monitoring device of claim 1, wherein the processing unit is configured to operate the monitoring device in a combined mode by selectively operating one or more of the radiation sources and one or more of the detectors such that the radiation sources and the detectors are disposed on at least two sides of a region of interest of the subject to simultaneously measure reflectance and transmission signals.

24. The monitoring device of claim 1, wherein the processing unit is configured to generate an audio output, a visual output, an alert message, or combinations thereof, if the quality metric associated with a physiological parameter is outside a corresponding designated threshold.

25. The monitoring device of claim 24, wherein the processing unit is configured to terminate the audio output, the visual output, the alert message, or combinations thereof, if the quality metric associated with a physiological parameter is within a corresponding designated threshold.

26. The monitoring device of claim 1, wherein the processing unit is further configured to:
select the one or more other wavelengths that minimize an effect of a wavelength shift in one or more of the radiation sources during multi-analyte measurements corresponding to the one or more physiological parameters;
determine optical path length data corresponding to each of the one or more other selected wavelengths, wherein the determined optical path length data accounts for non-linearity of photon transport through a target tissue of the subject while performing the multi-analyte measurements;
determine the configuration of the operational geometry of the sensor for the one or more other wavelengths based on die determined optical path length data and the baseline operating configuration; and
operate one or more of the radiation sources and detectors as large area devices, distributed devices, or a combination thereof, in the determined configuration, wherein the determined configuration maximizes optical generation and light capture efficiency, while reducing tissue motion artifacts.

27. A method for monitoring a subject, comprising:
selecting an initial set of one or more radiation sources and one or more detectors for an initial wavelength from a plurality of radiation sources and detectors disposed on a flexible substrate in a sensor in a designated physical arrangement;
determining an initial value of one or more physiological parameters of a subject by evaluating a region of interest of the subject using the initial set of radiation sources and detectors and the initial wavelength;
estimating a quality metric associated with the initial value of the physiological parameters; and
dynamically configuring an initial operational geometry of the sensor for the initial wavelength by controlling intensity of one or more of the radiation sources, gain of one or more of the detectors, or a combination thereof, until a threshold value of to satisfy at least one quality metric associated with the one or more physiological parameters of the subject is satisfied;
determining a revised configuration of operational geometry of the sensor for each of plural additional wavelengths that maximizes the quality metric using Monte Carlo simulations at each of the plural additional wavelengths, wherein the processing unit is configured to perform the Monte Carlo simulations to determine resulting signal quality based on placement of the radiation sources and detectors for plural configurations and to select the revised configuration based on the determined resulting signal quality; and
obtaining multiple measurements of the one or more physiological parameters at each of the plural additional wavelengths using the corresponding revised determined configuration for each of the plural additional wavelengths, without physically moving the sensor to a different measurement position.

28. The method of claim 27, wherein dynamically configuring the operational geometry of the sensor comprises:
iteratively selecting the one or more further radiation sources and detectors from the plurality of radiation sources and the one or more detectors;
determining corresponding values of one or more physiological parameters by evaluating the region of interest of the subject using the one or more further radiation sources and detectors for each iteration;
estimating the quality metric associated with the values of the physiological parameters determined using the one or more further radiation sources and detectors; and
adaptively reconfiguring the operational geometry of the sensor until the quality metric associated with the values of the physiological parameters determined in a particular iteration is within a designated threshold.

29. The method of claim 28, further comprising:
continuously monitoring the one or more physiological parameters of the subject using the radiation sources and detectors used in the particular iteration
periodically estimating the quality metric associated with the values of the physiological parameters; and
adaptively configuring the operational geometry of the sensor until the quality metric associated with the values of the physiological parameters is within the designated threshold.

30. A non-transitory computer readable medium that stores instructions executable by one or more processors to perform a method for monitoring a subject, comprising:
selecting an initial set of one or more radiation sources and one or more detectors for an initial wavelength from a plurality of radiation sources and detectors disposed on a flexible substrate in a sensor in a designated physical arrangement;
determining an initial value of one or more physiological parameters of a subject by evaluating a region of interest of the subject using the initial set of radiation sources and detectors and the initial wavelength;
estimating a quality metric associated with the initial value of the physiological parameters; and
dynamically configuring an initial operational geometry of the sensor for the initial wavelength by controlling intensity of one or more of the radiation sources, gain of one or more of the detectors, or a combination thereof, until a threshold value of to satisfy at least one quality metric associated with the one or more physiological parameters of the subject is satisfied;
determining a revised configuration of operational geometry of the sensor for each of plural additional wavelengths that maximizes the quality metric using Monte Carlo simulations at each of the plural additional wavelengths, wherein the processing unit is configured to perform the Monte Carlo simulations to determine resulting signal quality based on placement of the radiation sources and detectors for plural configurations and to select the revised configuration based on the determined resulting signal quality; and
obtaining multiple measurements of the one or more physiological parameters at each of the plural additional wavelengths using the corresponding revised determined configuration for each of the plural additional wavelengths, without physically moving the sensor to a different measurement position.

* * * * *